(12) United States Patent
Yuyama et al.

(10) Patent No.: US 7,822,505 B2
(45) Date of Patent: Oct. 26, 2010

(54) ARTICLE DISPENSING DEVICE AND METHOD

(75) Inventors: Shoji Yuyama, Osaka (JP); Akitomi Kohama, Osaka (JP); Takayuki Fujikawa, Osaka (JP)

(73) Assignee: Yuyama Mfg. Co., Ltd., Osaka (JP)

( * ) Notice: Subject to any disclaimer, the term of this patent is extended or adjusted under 35 U.S.C. 154(b) by 0 days.

(21) Appl. No.: 11/795,179

(22) PCT Filed: Jan. 11, 2006

(86) PCT No.: PCT/JP2006/000165

§ 371 (c)(1),
(2), (4) Date: Jul. 12, 2007

(87) PCT Pub. No.: WO2006/075583

PCT Pub. Date: Jul. 20, 2006

(65) Prior Publication Data

US 2008/0083769 A1    Apr. 10, 2008

(30) Foreign Application Priority Data

Jan. 13, 2005  (JP)  ............................. 2005-006390
Jan. 10, 2006  (JP)  ............................. 2006-002534

(51) Int. Cl.
*G06F 17/00* (2006.01)

(52) U.S. Cl. ...................... 700/242; 700/231; 700/232; 221/206; 221/224; 221/226; 221/127

(58) Field of Classification Search ......... 700/231–244; 221/1–312 C, 206, 224, 226, 127
See application file for complete search history.

(56) References Cited

U.S. PATENT DOCUMENTS 5,292,029 A * 3/1994 Pearson ......................... 221/2
5,337,919 A    8/1994 Spaulding et al.
5,671,592 A    9/1997 Yuyama et al.

(Continued)

FOREIGN PATENT DOCUMENTS

JP    02-083186 A    3/1990

(Continued)

OTHER PUBLICATIONS

Image File Wrapper for U.S. Publication No. 2008/0271414.

*Primary Examiner*—Gene Crawford
*Assistant Examiner*—Michael K Collins
(74) *Attorney, Agent, or Firm*—Patterson Thuente Christensen Pedersen, P.A.

(57) ABSTRACT

To dispense an article in a limited space within a tray appropriately with no useless operation, the present invention provides an article dispensing device, including a control means (61) which calls, from a storage means (64), an article map of an article (D) to be dispensed by a dispensing means (3) and a container map of a container (5) for accommodating the article (D), which searches for a vacant region by searching each container virtual region of the container map in a predetermined order, which specifies a dispensing position for the article (D) according to the article map, and which drive-controls the dispensing means (3) based on the specified dispensing position for causing the article (D) held to be accommodated in the container (5).

8 Claims, 18 Drawing Sheets

U.S. PATENT DOCUMENTS

| | | |
|---|---|---|
| 5,771,657 A | 6/1998 | Lasher et al. |
| 5,930,145 A | 7/1999 | Yuyama et al. |
| 6,006,946 A | 12/1999 | Williams et al. |
| 6,119,737 A * | 9/2000 | Yuyama et al. ............. 141/104 |
| 6,349,848 B1 | 2/2002 | Uema et al. |
| 6,625,952 B1 * | 9/2003 | Chudy et al. ................. 53/168 |
| 6,739,476 B2 * | 5/2004 | Shigeyama et al. ......... 221/172 |
| 6,742,671 B2 | 6/2004 | Hebron et al. |
| 6,748,295 B2 * | 6/2004 | Tilles et al. ................. 700/241 |
| 6,962,267 B2 * | 11/2005 | Herzog et al. ................. 221/85 |
| 7,086,560 B2 * | 8/2006 | Shioya ....................... 221/191 |
| 7,123,989 B2 * | 10/2006 | Pinney et al. ............... 700/237 |
| 7,234,609 B2 * | 6/2007 | DeLazzer et al. ............. 221/10 |
| 7,562,791 B2 | 7/2009 | Yuyama et al. |
| 2003/0187692 A1 | 10/2003 | Park |
| 2005/0131578 A1 * | 6/2005 | Weaver ....................... 700/244 |
| 2005/0192705 A1 * | 9/2005 | Pinney et al. ............... 700/241 |
| 2006/0074523 A1 * | 4/2006 | Chirnomas .................. 700/232 |
| 2007/0150092 A1 | 6/2007 | Ohmura et al. |
| 2008/0065264 A1 * | 3/2008 | Omura et al. ............... 700/231 |
| 2008/0271414 A1 | 11/2008 | Yuyama et al. |

FOREIGN PATENT DOCUMENTS

| | | |
|---|---|---|
| JP | 03-242147 | 10/1991 |
| JP | 10-077107 | 3/1998 |
| JP | 11-070901 | 3/1999 |
| JP | 11-208604 A | 8/1999 |
| JP | 2002-120913 A | 4/2002 |
| JP | 2002-126044 | 5/2002 |
| JP | 2002-272812 | 9/2002 |
| JP | 2002-370701 | 12/2002 |
| JP | 2003-044940 | 2/2003 |
| JP | 2003-118816 | 4/2003 |
| JP | 2003-146414 | 5/2003 |
| JP | 2003-206024 | 7/2003 |
| JP | 2003-237703 | 8/2003 |
| JP | 2003-237711 | 8/2003 |
| JP | 2003-530650 | 10/2003 |
| JP | 2004-157579 | 6/2004 |
| JP | 2004-187958 | 7/2004 |
| JP | 2004-256242 | 9/2004 |
| JP | 2005-122360 | 5/2005 |
| JP | 2005-192702 | 7/2005 |
| WO | WO 01/77927 | 10/2001 |
| WO | WO 2004/014288 | 2/2004 |
| WO | WO 2004/014734 | 2/2004 |

* cited by examiner

Figure 3
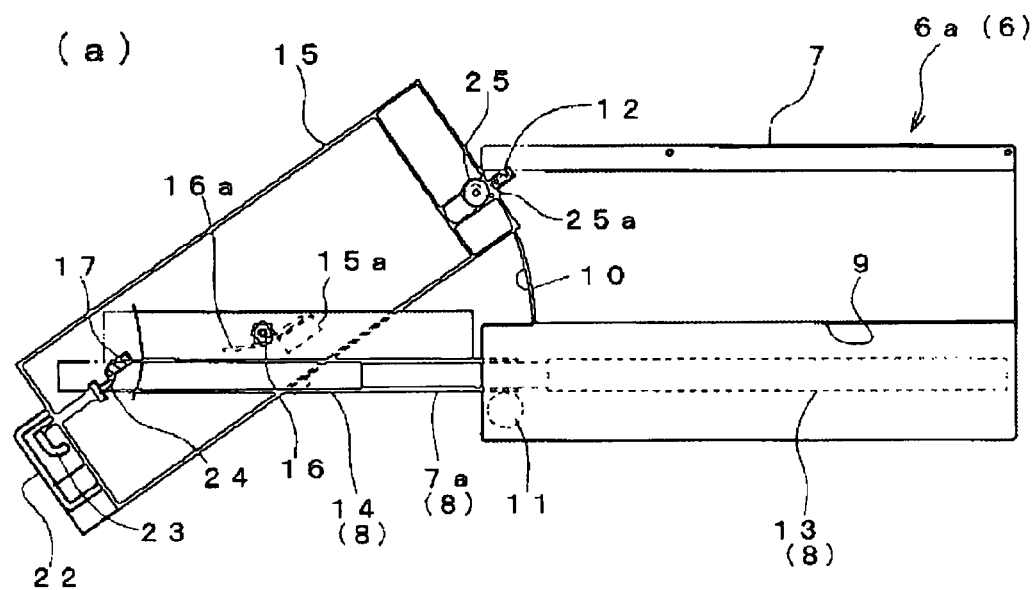
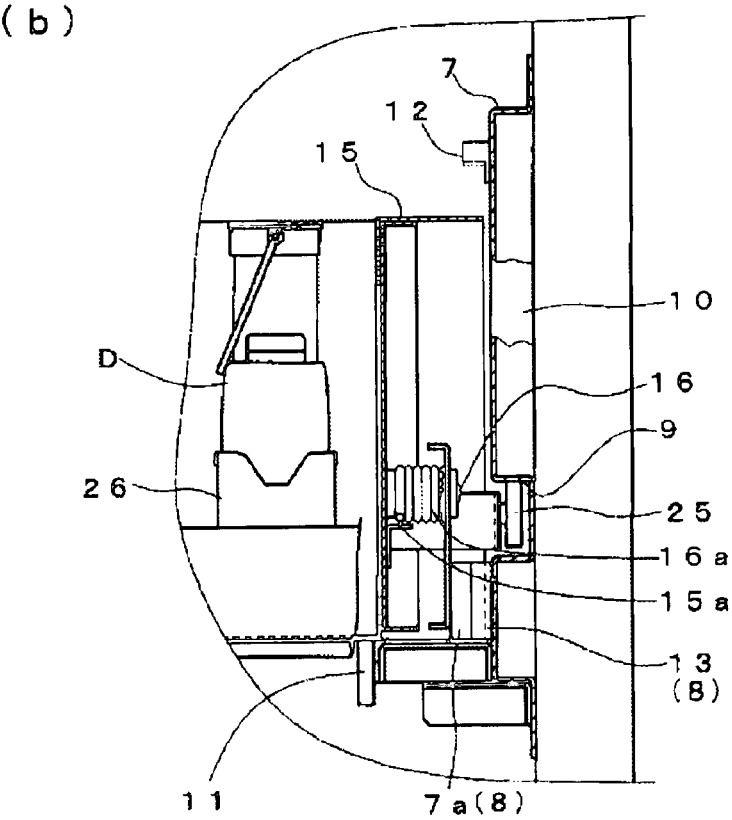

Figure 10
(a)
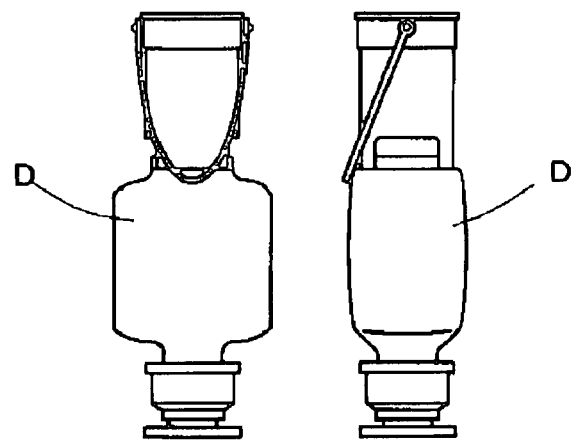
(b)
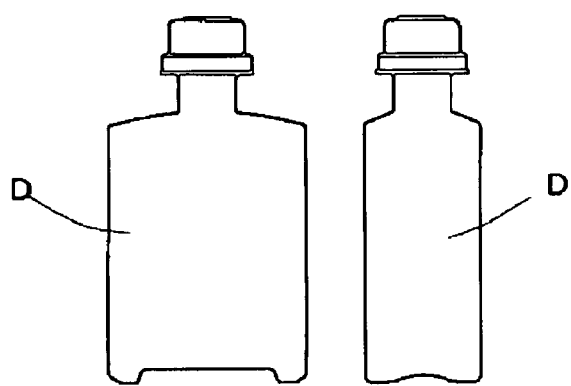
(c)
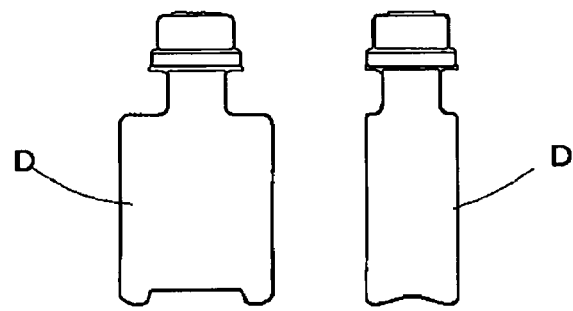

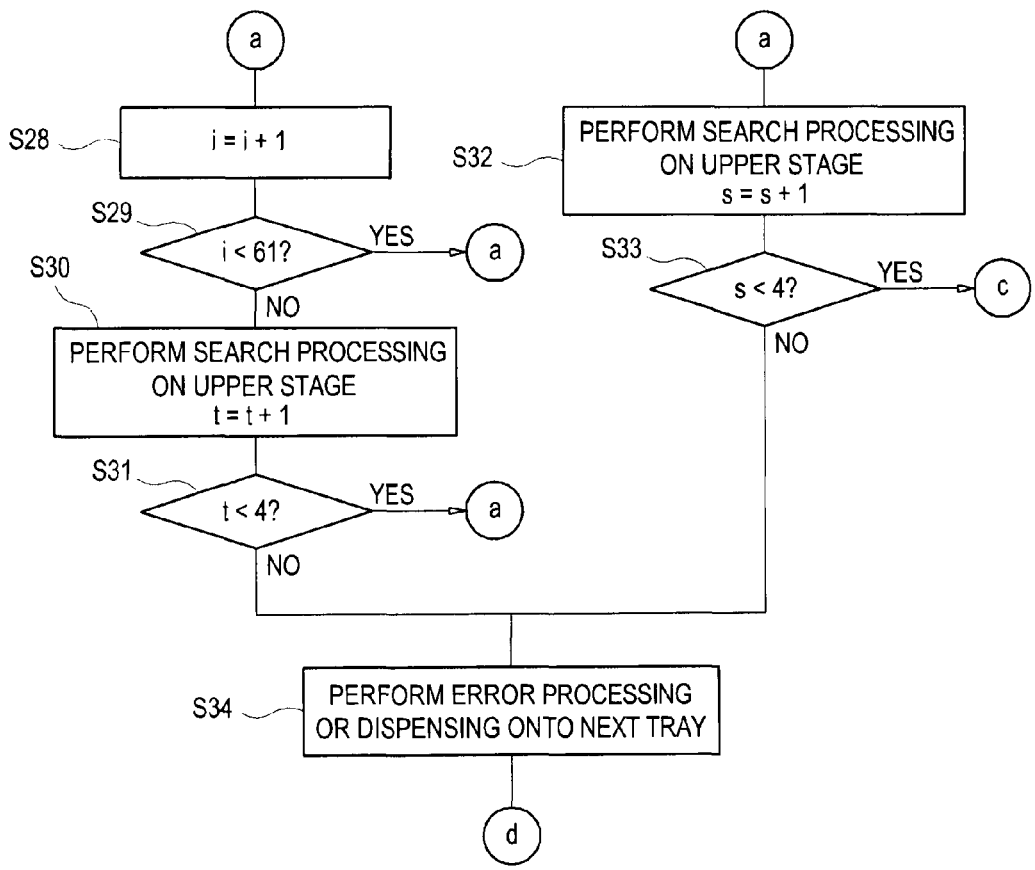

Figure 17
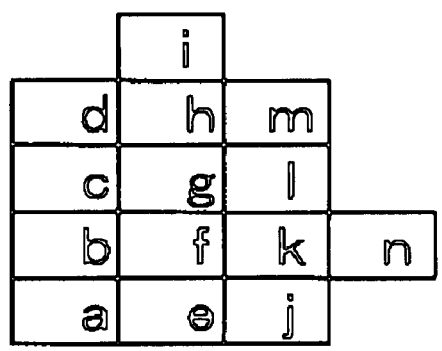
Figure 18
| 5 | 10 | 15 | 20 | 25 | 30 | 35 | 40 | 45 | 50 | 55 | 60 |
|---|----|----|----|----|----|----|----|----|----|----|----|
| 4 | 9  | 14 | 19 | 24 | 29 | 34 | 39 | 44 | 49 | 54 | 59 |
| 3 | 8  | 13 | 18 | 23 | 28 | 33 | 38 | 43 | 48 | 53 | 58 |
| 2 | 7  | 12 | 17 | 22 | 27 | 32 | 37 | 42 | 47 | 52 | 57 |
| 1 | 6  | 11 | 16 | 21 | 26 | 31 | 36 | 41 | 46 | 51 | 56 |
Figure 19
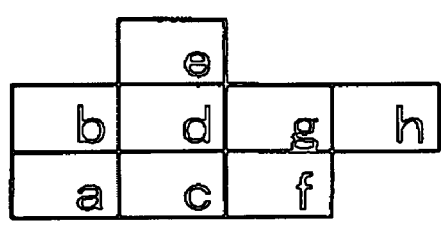

ARTICLE DISPENSING DEVICE AND METHOD

CROSS REFERENCE TO THE RELATED APPLICATIONS

The present application is a National Phase entry of PCT Application No. PCT/JP06/00165, filed Jan. 11, 2006, which claims priority from Japanese Application Number 2005-006390, filed Jan. 13, 2005, and Japanese Application Number 2006-002534, filed Jan. 10, 2006, the disclosures of which are hereby incorporated by reference herein in their entirety.

TECHNICAL FIELD

The present invention relates to an article dispensing device for dispensing mainly a drug to a predetermined position in a tray.

BACKGROUND ART

Conventionally, there has been disclosed an allocating system making it possible to appropriately allocate a commodity to be supplied into a tray (see, for example, Patent Document 1). In this allocating system, various kinds of allocating conditions are stored in an allocating server, and the allocating pattern for the tray is determined in conformity with prescription data. Patent Document 1: JP 2002-120913 A

SUMMARY OF THE INVENTION

However, in the above-mentioned allocating system, the interior of the tray is simply divided into a plurality of sections beforehand, merely deciding the section where the commodity supplied is to be accommodated. Thus, depending on differences in the size and configuration of the sections, the kind of commodity that can be accommodated is restricted. Further, this system is liable to involve inutile space. That is, the above-mentioned allocating system is not of a dispensing construction allowing accommodation of commodities in the tray at high density.

In view of this, it is an object of the present invention to provide an article dispensing device that is capable of dispensing articles such that they can be accommodated in the limited space in the tray appropriately without involving any inutile space.

As means for solving the problems described above, the present invention provides an article dispensing device including: a dispensing means for holding an article and dispensing it into a container; a storage means for storing a container map prepared by dividing an internal space of the container into a plurality of container virtual regions, and an article map prepared by dividing the article into a plurality of article virtual regions that are in a predetermined correlation with the container virtual regions; and a control means which calls from the storage means the article map of the article to be dispensed by the dispensing means and the container map of the container for accommodating the article, which searches for a vacant region by searching each container virtual region of the container map in a predetermined order, which specifies a dispensing position for the article according to the article map, and which drive-controls the dispensing means based on the specified dispensing position for causing the article held to be accommodated in the container.

With the above construction, it is possible to search for a vacant region by successively searching the container virtual regions forming the container map in terms of the article virtual regions, enabling to specify the dispensing position for the articles and to dispense the articles into the container at high density.

The above-mentioned predetermined correlation may imply that the container virtual regions and the article virtual regions are of the same size, that a container virtual region is of a size corresponding to that of a combination of a plurality of article virtual regions, or that an article virtual region is of a size corresponding to that of a combination of a plurality of container virtual regions.

When the article map stored in the storage means is provided with at least a stick-out region sticking out beyond the actual article size by an amount corresponding to one article virtual region, it is possible to reliably avoid interference between the articles. This is preferable in the point that it is possible to realize a smooth dispensing operation.

The container may have an internal space capable of accommodating articles vertically in a plurality of stages, in which the container map stored in the storage means is formed by a container virtual space formed of a three-dimensional space sectioned also vertically in correspondence with the accommodation structure of the container, with the article map being formed by an article virtual space of the same size as the container virtual space, and in which, when it is judged that the article map of the article to be contained in the container occupies a plurality of vertically sectioned container virtual spaces of the container map, the control means searches for a vacant region in the container map, and, after checking for a vacant region on a lowermost stage, also checks for a vacant region on a corresponding upper stage, and settles on a dispensing position only when it is judged that vacant regions exist on both stages.

With this construction, the internal space of the container is considered in a three-dimensional terms, making it possible to dispense articles stacked together in a plurality of stages.

As the configuration of the virtual regions, it is possible to adopt various planar configurations such as a square, rectangular, or triangular configuration. Apart from this, it is also possible to adopt various three-dimensional configurations, such as a cubic or parallelepiped configuration.

According to the present invention, the internal space of a container and an article are divided into virtual regions of the same size, and a vacant region is searched for to specify a dispensing position for the articles, whereby it is possible to dispense the articles into the container without involving much inutile space.

BRIEF DESCRIPTION OF THE DRAWINGS

FIG. 3 includes portion (a) showing a detailed view of the draw-out structure of the shelf member of FIG. 2, and portion (b) showing an enlarged partial side sectional view.

FIGS. 10 are diagrams showing examples of the drug accommodated in the cassette.

FIG. 15B is a flowchart illustrating the dispensing processing of FIG. 14.

FIG. 16 is a diagram showing an example of the container map.

FIG. 17 is a diagram showing an example of the drug map.

FIG. 18 is a diagram illustrating how the drug map shown in FIG. 17 is applied to the container map of FIG. 16.

FIG. 19 is a diagram showing another example of the drug map.

DETAILED DESCRIPTION OF THE INVENTION

In the following, an embodiment of the present invention will be described with reference to the accompanying drawings.

Figure 1:
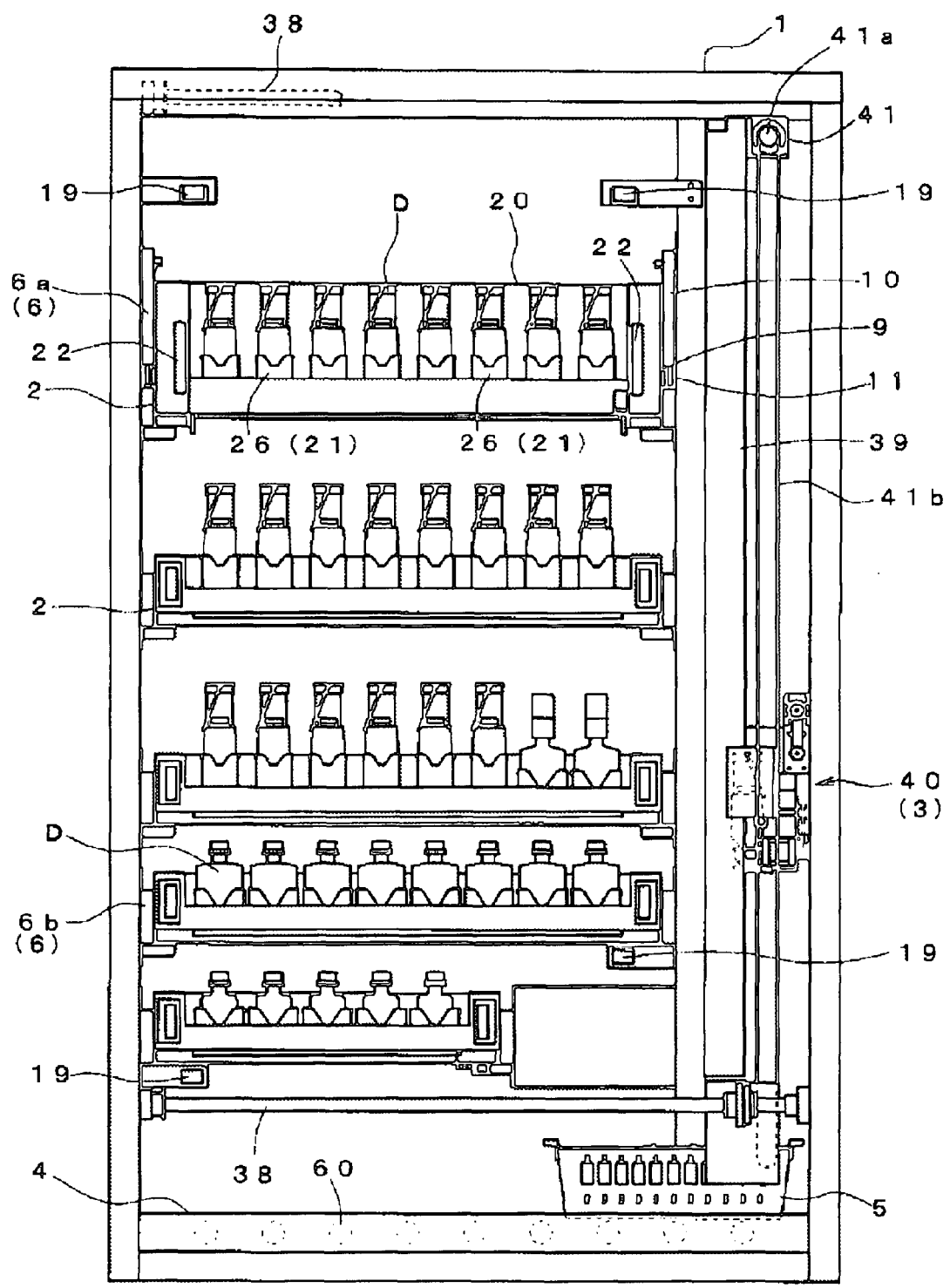
FIG. 1 is a front view of a drug supply device according to this embodiment of the present invention.
Figure 2:
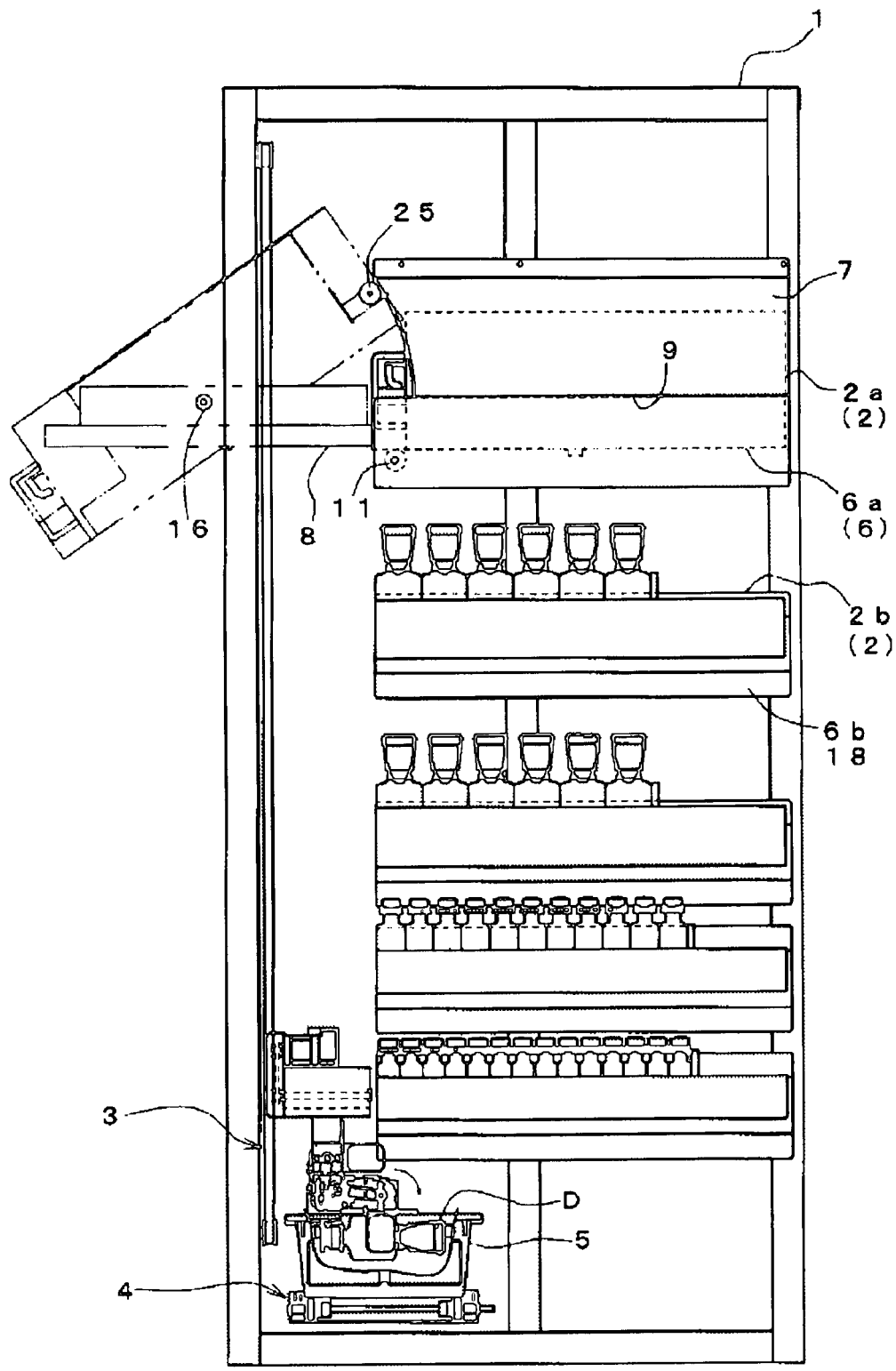
FIG. 2 is a side view of FIG. 1.

FIG. 1 is a front view of a drug dispensing device according to this embodiment, and FIG. 2 is a side view thereof. In this drug dispensing device, a plurality of shelf members 2 are arranged vertically side by side within a device main body 1, and drugs D accommodated in the shelf members 2 are conveyed downwards by a dispensing means provided on the front side of the device main body 1, that is, a drug conveying member 3, and are accommodated in a tray 5 conveyed along a tray conveying line 4.

The front side of the device main body 1 is opened and closed by a door (not shown), and a plurality of guide members 6 are provided on the inner surfaces of the side walls thereof. The guide members 6 is composed of a first guide member 6a situated uppermost, and a second guide member 6b situated below the same.

As shown in FIGS. 2 and 3, the first guide member 6a is equipped with a guide wall 7, and a guide rail 8 supported by the inner surface of the guide wall 7 so as to be slidable in the longitudinal direction (horizontal direction of FIG. 2).

The guide wall 7 has a horizontally extending first guide surface 9 formed at the lower edge of the upper half thereof, and an arcuate second guide surface 10 formed at the forward end surface of the upper half thereof; on the front side of the lower half thereof, a support roller 11 is rotatably arranged. On the second guide surface 10, there is provided a stopper 12 which is abutted by a protrusion 25a provided in the vicinity of a guide roller 25 of the shelf member 2 described below to prevent further rotation of the shelf member 2. In the guide rail 8, an intermediate rail portion 7a is slidably provided on a first rail portion 13 integrated with the guide wall 7, and a second rail portion 14 is slidably provided on the intermediate rail portion 7a, whereby the second rail portion 14 can reciprocate in the longitudinal direction of the device main body 1. A support wall 15 is formed above the second rail portion 14. At the center of the support wall 15, there is provided a support shaft 16 rotatably supporting the shelf member 2. Around the support shaft 16, there is provided a spring 16a, one end of which is fixed to the support wall 15, and the other end of which abuts an abutment/receiving portion 15a formed on the shelf member 2, whereby the shelf member 2 is urged in the horizontal direction. Further, on the front side of the support wall 15, there is formed a locking/receiving portion 17, to which a lock portion 24 of a lock member 23 provided on the shelf member 2 is locked, whereby the shelf member 2 is prevented from rotating and is placed in a tilted state.

As shown in FIGS. 1 and 2, the second guide member 6b is equipped with a support rail portion 18 supporting the shelf member 2 so as to allow it to slide in the longitudinal direction of the device main body 1. In the second guide member 6b, the shelf member 2 is just supported so as to be capable of reciprocating in the horizontal direction.

As shown in FIG. 1, in the upper and lower portions of both side walls of the device main body 1, there are provided shelf positional deviation detecting sensors 19 (In this embodiment, two sets of sensors are provided at upper and lower positions, with each set being equipped with a light emitting element and a light receiving element). The shelf positional deviation sensors 19 make a detection as to whether the shelf members 2 are being left drawn out or not. That is, the shelf members 2 have through-holes so light can pass therethrough from the light emitting elements to the light receiving elements, with the shelf members 2 being accommodated in appropriate positions in the device main body 1.

As shown in FIG. 1, each shelf member 2 is formed of a box body 20 whose upper surface is open and whose front side is cut out and in which a plurality of rows of drug accommodating portions 21 are formed in the width direction, with grips 22 being provided at both ends of the front side of the box body 20. The shelf members 2 are composed of a first shelf member 2a situated uppermost and supported by the first guide member 6a, and a second shelf member 2b situated below the same and supported by the second guide member 6b.

As shown in FIG. 2, the first shelf member 2a is supported by the guide wall 7 of the device main body 1 so as to be rotatable around the support shaft 16, and is urged horizontally by the spring 16a. As shown in FIG. 3, the lock member 23 is provided in the vicinity of one grip 22, with the lock portion 24 thereof being detachable with respect to the locking/receiving portion 17 of the support wall 15. The lock portion 24 is locked to the locking/receiving portion 17, whereby the first shelf member 2a is maintained in the tilted state as shown in FIG. 3. Further, the guide roller 25 is rotatably provided on the back side of the first shelf member 2a. The guide roller 25 rolls on the first guide surface 9 and the second guide surface 10 formed on the guide member 6 of the device main body 1. Each drug accommodating portion 21 is formed of a cassette 26 in which a drug extrusion member 30 is provided.

The second shelf member 2b is supported by the second guide member 6b so as to be slidable exclusively in the horizontal direction.

Figure 4:
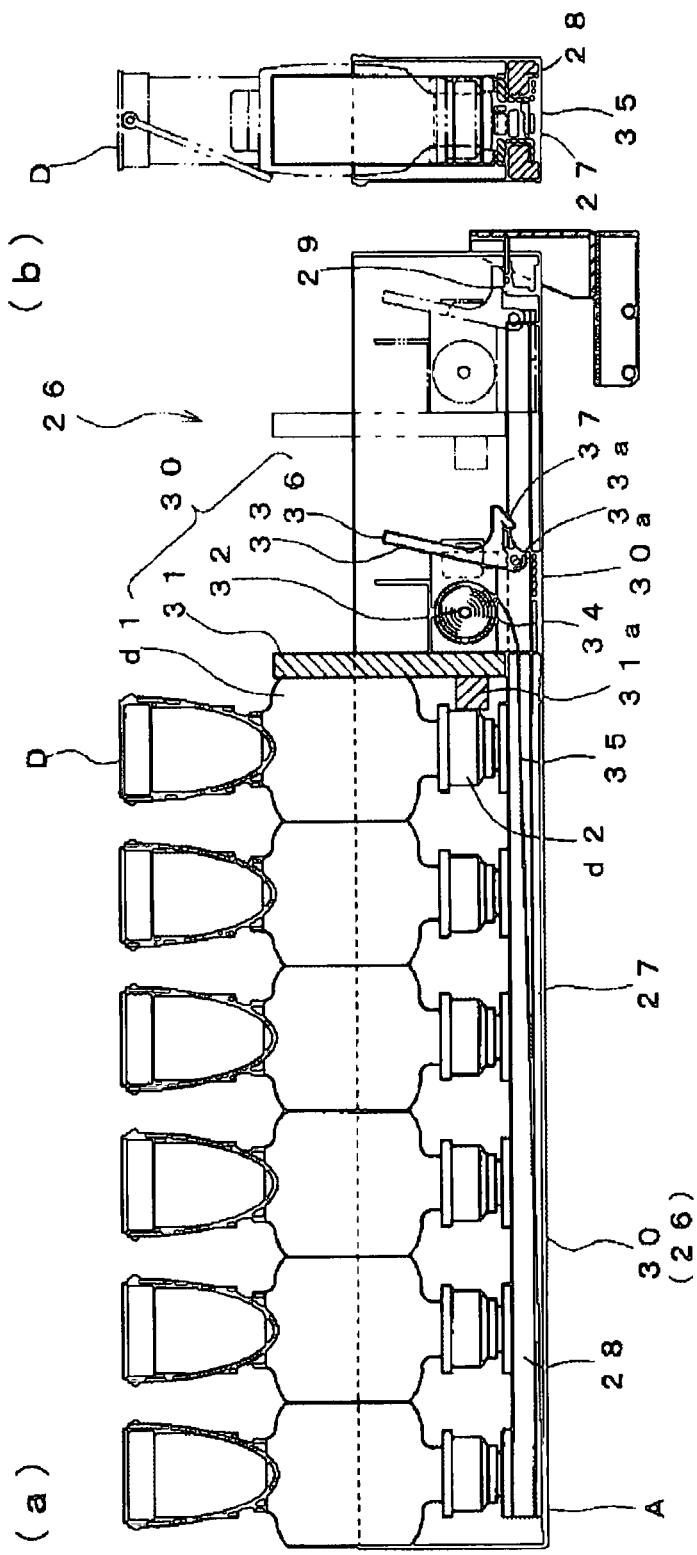
FIG. 4 includes portion (a) showing a sectional view of a cassette arranged in the shelf member shown in FIG. 3, and portion (b) showing a side sectional view thereof.

As shown in FIG. 4, the cassette 26 is formed as a box which is open at the upper surface and which can accommodate drugs D aligned in a single row such that portions of their upper surfaces (e.g., their upper halves) are exposed. At the bottom surface of the cassette 26, there is arranged a support plate 28 elongated on both sides so as to form a longitudinal groove portion 27. As a result, it is possible to decrease in the contact area with the drugs D accommodated in the cassette 26 and to position a spring portion 35 of a constant force spring 32 in the groove portion 27. Further, at the rear end of the cassette 26, there is formed a lock hole 29 to which a lock portion 37 of a lock lever 33 described below is to be locked. While each cassette 26 can be formed in the same size for the same box body 20 to accommodate drugs D of the same form, it is also possible, if there is a change in size (e.g., change in the distance between the side walls or the height of the side walls), for the cassette 26 to accommodate drugs D of some other form.

As shown in FIGS. 4(a) and 4(b), the drug extrusion member 30 is formed by providing in a casing 30a a pusher 31, the constant force spring 32, and the lock lever 33.

The casing 30a is arranged at the bottom surface of the cassette 26 so as to be slidable in the longitudinal direction thereof.

The pusher 31 is formed as a plate fixed to the end surface of the casing 30a and capable of pressurizing the side surfaces of the drugs D. Here, in order to support a body portion d1 of a drug D which has the form as shown in FIGS. 4(a) and 10(a) and a leg portion d2 thereof, which is thinner than the body portion d1, a protrusion 31a is provided on the abutment surface to form a stepped configuration. As shown in FIGS. 10(b) and 10(c), the drugs D may assume various forms and, by varying the configuration of the pusher 31 according to their form, it is possible to pressurize the drugs smoothly in the horizontal direction.

As shown in FIG. 4(a), the constant force spring 32 is composed of a drum 34 arranged within the casing 30a, and a spring portion 35 formed by winding an elongated strip plate around the drum 34. In the constant force spring 32, the spring portion 35 drawn out of the casing 30a is drawn into the casing 30a with a fixed force regardless of the draw-out dimension. The spring portion 35 is situated in the groove portion 27 formed on the bottom surface of the cassette 26, and a forward end A of the spring portion 35 is fixed to the front end surface of the cassette 26. In this embodiment, as the constant force spring 32, there is used Conston (registered trademark) or the like, which is commercially available.

The lock lever 33 is provided rotatably around a shaft portion 33a; one end of the lock lever 33 is an operating portion 36 to be directly operated by a finger, and the other end thereof is the lock claw 37 that is detachable with respect to the lock hole 29 formed at the rear end of the cassette 26.

As shown in FIG. 1, the drug conveying member 3 is equipped with a horizontal guide bar 38, a vertical guide bar 39, and a drug grasping member 40.

Figure 11:
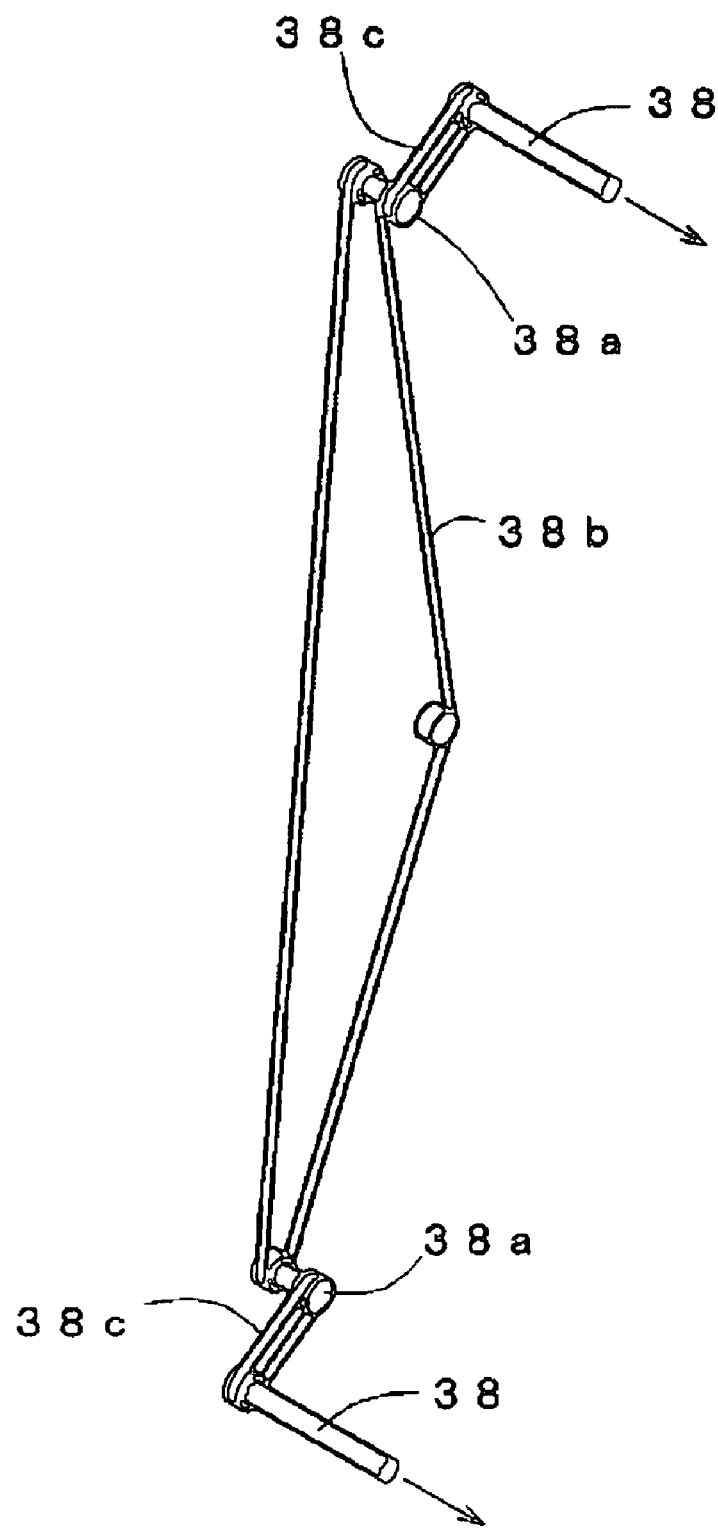
FIG. 11 is a schematic explanatory view illustrating how the horizontal guide bar shown in FIG. 1 is driven.

The horizontal guide bars 38 are arranged on each of the upper and lower front sides of the device main body 1, and extend horizontally to the right and left as shown in the drawing. The two horizontal guide bars 38 rotate in synchronism with each other via pulleys 38a and belts 38b, 38c shown in FIG. 11. Each horizontal guide bar 38 is formed by a screw. The upper and lower end portions of the vertical guide bar 39 are threadedly engaged with the horizontal guide bars 38; through normal and reverse rotation of the horizontal guide bars 38 by driving a motor (not shown), the vertical guide bar 39 reciprocates along the horizontal guide bars 38. At the upper end of the vertical guide bar 39, there is provided a drive motor 41, which raises and lowers, via a pulley 41a and a belt 41b, the drug grasping member 40 connected to a midpoint of the belt 41b.

As shown in FIGS. 5 through 8, in the drug grasping member 40, a longitudinal movement member 43 is provided on a support member 42 so as to be capable of reciprocating, and a holding member 44 is provided on the longitudinal movement member 43 so as to be capable of swiveling.

The support member 42 is equipped with side wall portions 42a, 42b whose upper portions are connected together; a guide receiving portion 45 is provided in the inner surface of one side wall portion 42a, and a first guide shaft 46 and a first screw 47 are provided parallel to the other side wall portion 42b. The first screw 47 rotates via the pulley 48a and the belt 48b through the driving of the first motor 48.

In the longitudinal movement member 43, there are provided side plate portions 50 on both sides of a slide stand 49 so as to be opposed to each other; on the slide stand 49, there is provided a roller 49a adapted to roll in the guide receiving portion 45 of the support member 42. Further, the first guide shaft 46 passes through the slide stand 49 which is threadedly engaged with the first screw 47. When the first screw 47 is rotated through normal and reverse rotation of the first motor 48, the thread-engagement position on the slide stand 49 changes, and the slide stand 49, that is, the longitudinal movement member 43, reciprocates along the first guide shaft 46.

Figure 7:
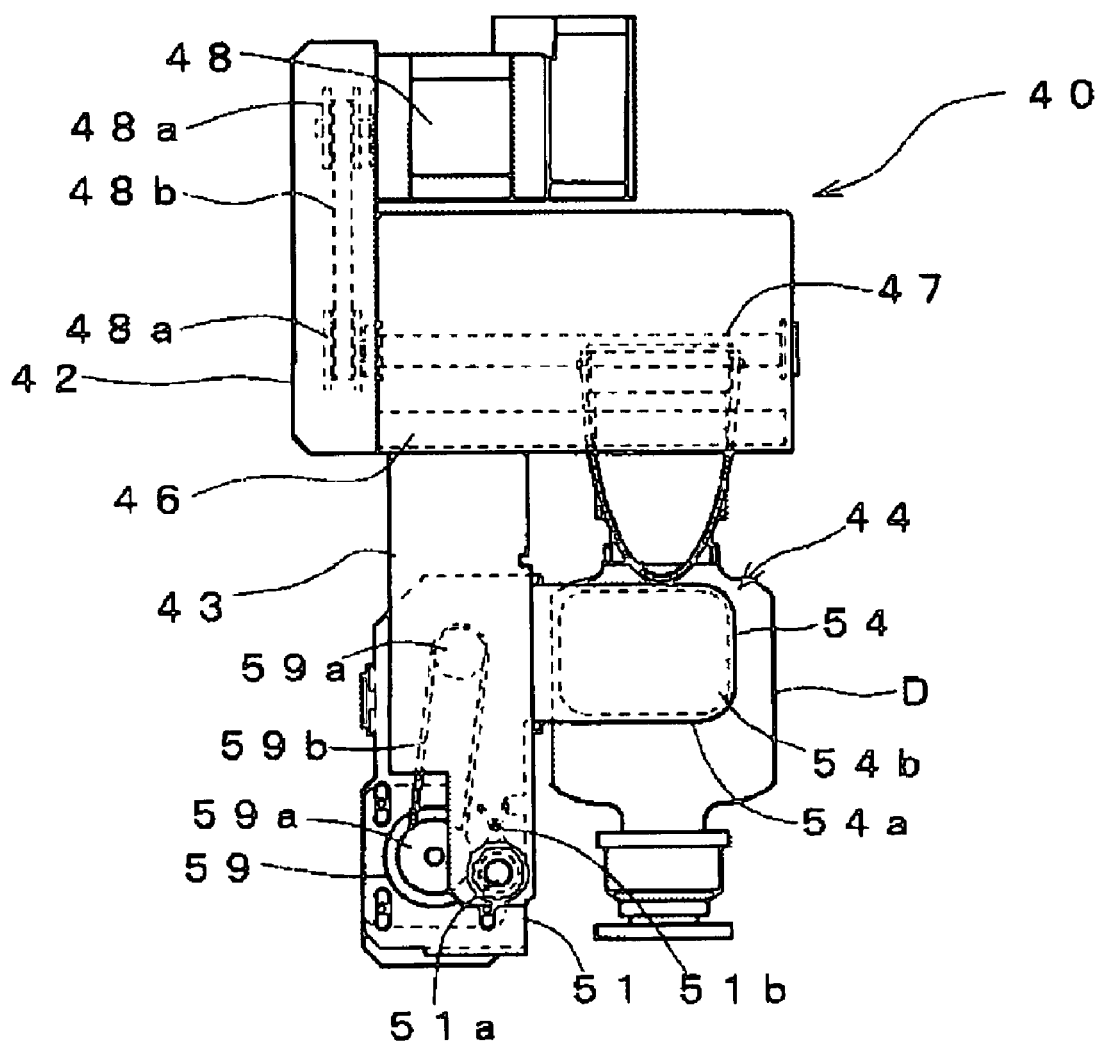
FIG. 7 is a side view of FIG. 5.
Figure 8:
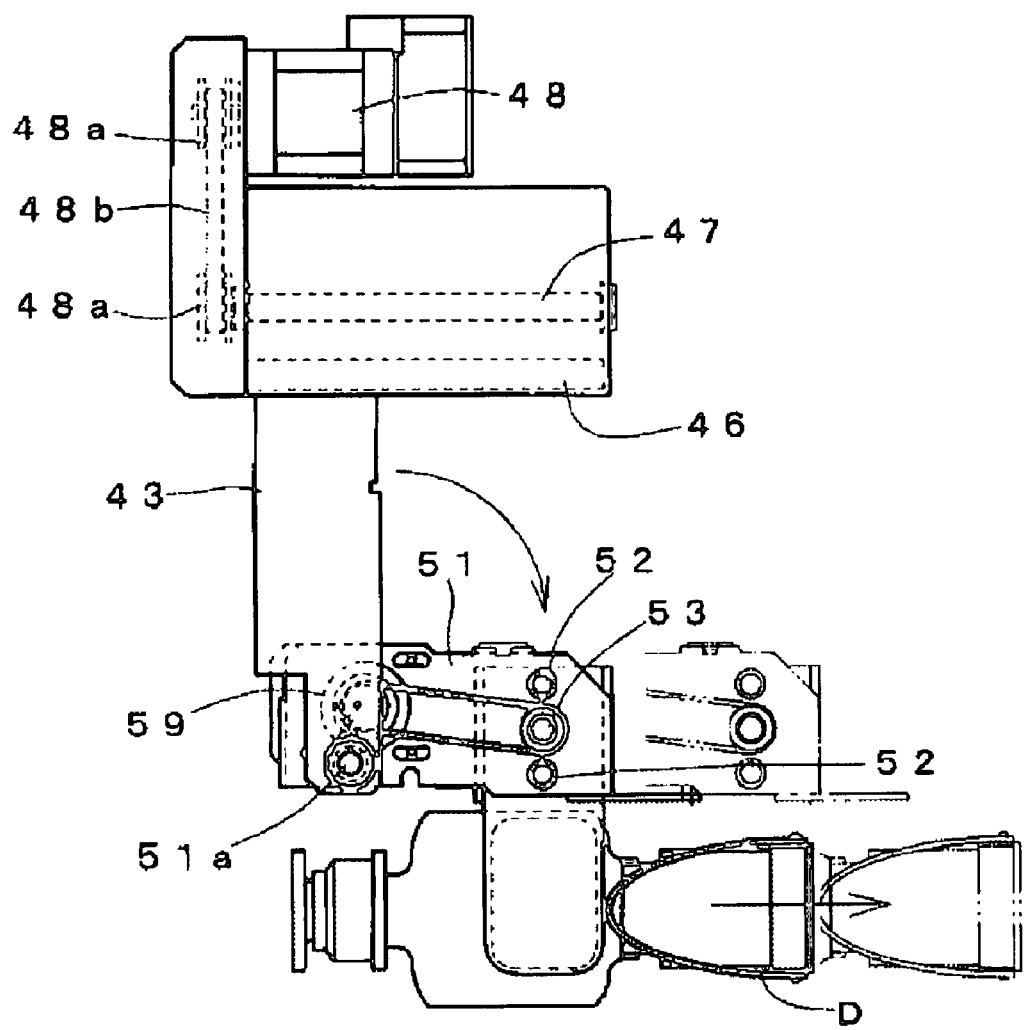
FIG. 8 is a diagram showing how the swiveling plate is rotated from the position of FIG. 7.

The holding member 44 includes a pair of swiveling plates 51, a second guide shaft 52 and a second screw 53 provided between the swiveling plates 51, and a pair of holding members 54 through which the second guide shaft 52 passes and with which the second screw 53 is threadedly engaged. The swiveling plates 51 are mounted rotatably around a rotation shaft 51a provided on the side plate portion 50 of the longitudinal movement member 43. A spring 51b is arranged at either end of the rotation shaft 51a, and the swiveling plates 51 are urged so as to be set in a vertical position as shown in FIG. 7.

A pressure receiving member 55 extends horizontally from the lower end of one swiveling plate 51. As described below, when the drug conveying member 3 is moved to a predetermined position, the pressure receiving member 55 is pressurized by a pressurizing member provided in the device main body 1 (which, although not shown, corresponds to the pressurizing portion of the present invention). As a result, the swiveling plates 51, that is, the holding members 44, rotate, making it possible to lay down the drug D being held between the holding members 54.

Figure 9:
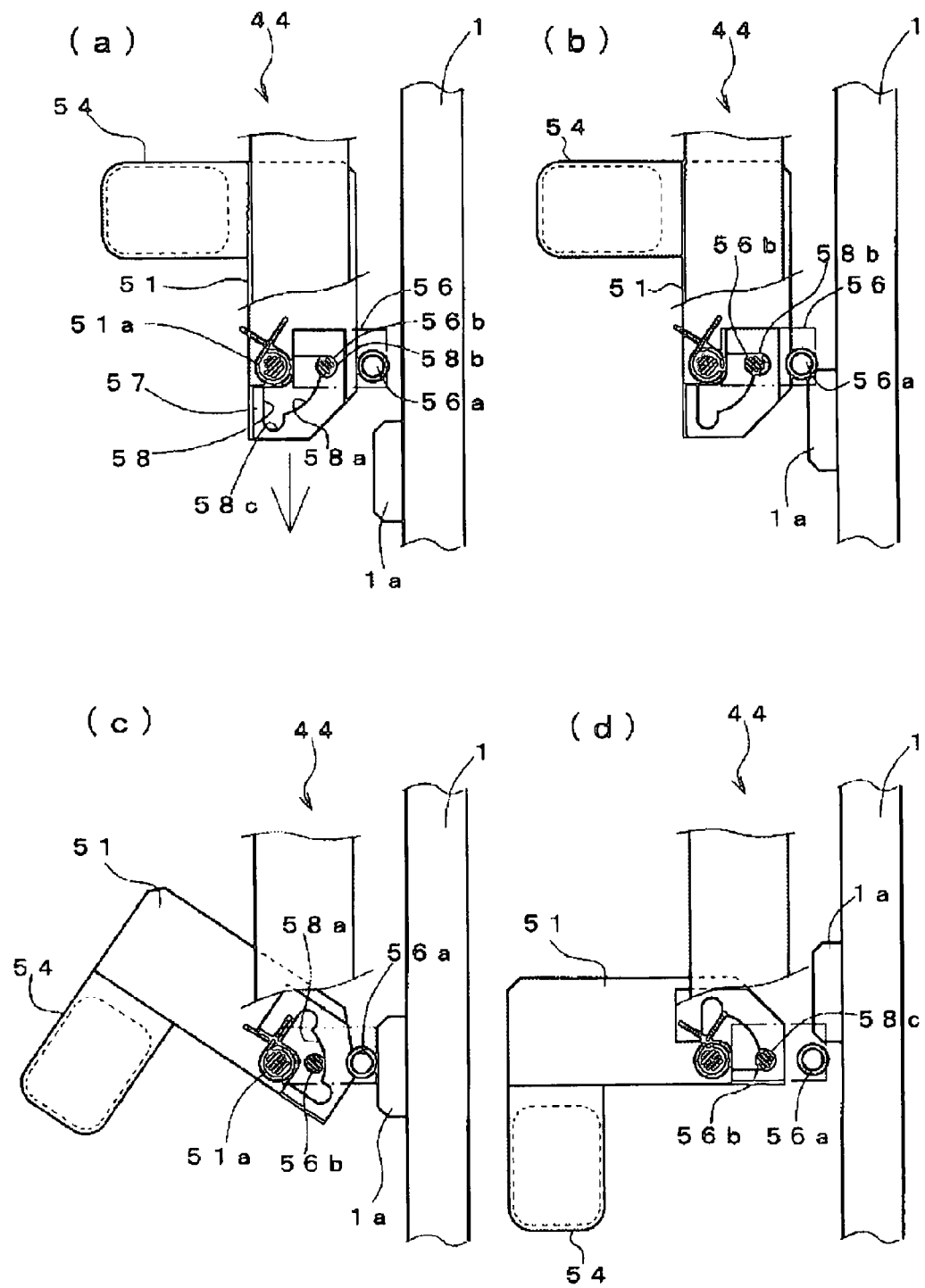
FIG. 9 is a diagram showing how the swiveling plate is swiveled.

Further, as shown in FIG. 9, at the lower end of the other swiveling plate 51, there is provided a first lock plate 56 so as to be capable of reciprocating while being urged in the horizontal direction (to the right in FIG. 9(a)) by a spring (not shown). Further, the first lock plate 56 is equipped with a roller 56a and a lock pin 56b. The roller 56a is pressurized by a protrusion 1a formed on the device main body 1, and reciprocates horizontally along the protrusion 1a. The lock pin 56b moves in a lock hole 58 of a second lock plate 57 integrated with the lower end portion of the swiveling plate 51. The lock hole 58 is formed in a sector-shape, and a first lock recess 58b and a second lock recess 58c are formed at each of the ends of the arcuate portion 58a thereof. When the holding members 44 descend, the roller 56a is pressurized by the protrusion 1a, and reciprocates against the urging force of the spring 51b, whereby the lock pin 56b is detached from the first lock recess 58b, and moves to the second lock recess 58c for engagement via the arcuate portion 58a. When the holding members 44 ascend, the roller 56a is pressurized by the protrusion 1a, and reciprocates against the urging force of the spring 51b, whereby the lock pin 56b is detached from the second lock recess 58c, and moves to the first lock recess 58b via the arcuate portion 58a.

The second guide shafts 52 are arranged on both sides on the same horizontal plane as the second screw 53. As a result, positional deviation in the rotational direction of the holding members 54 with respect to the second screws 53 is prevented, and they move smoothly toward and away from each other while protruding horizontally. In the second screw 53, the thread forming direction differs between the right-hand and left-hand sides (e.g., the left half is formed as a right-hand screw, and the right half is formed as a left-hand screw). Further, the second screw 53 makes normal and reverse rotation via the pulleys 59a and the belt 59b through normal and reverse rotation of the second motor 59. As a result, the threaded engagement positions of the holding members 54, which are threadedly engaged with the second screw 53, are changed, and the holding members 54 make parallel movements toward and away from each other.

Figure 5:
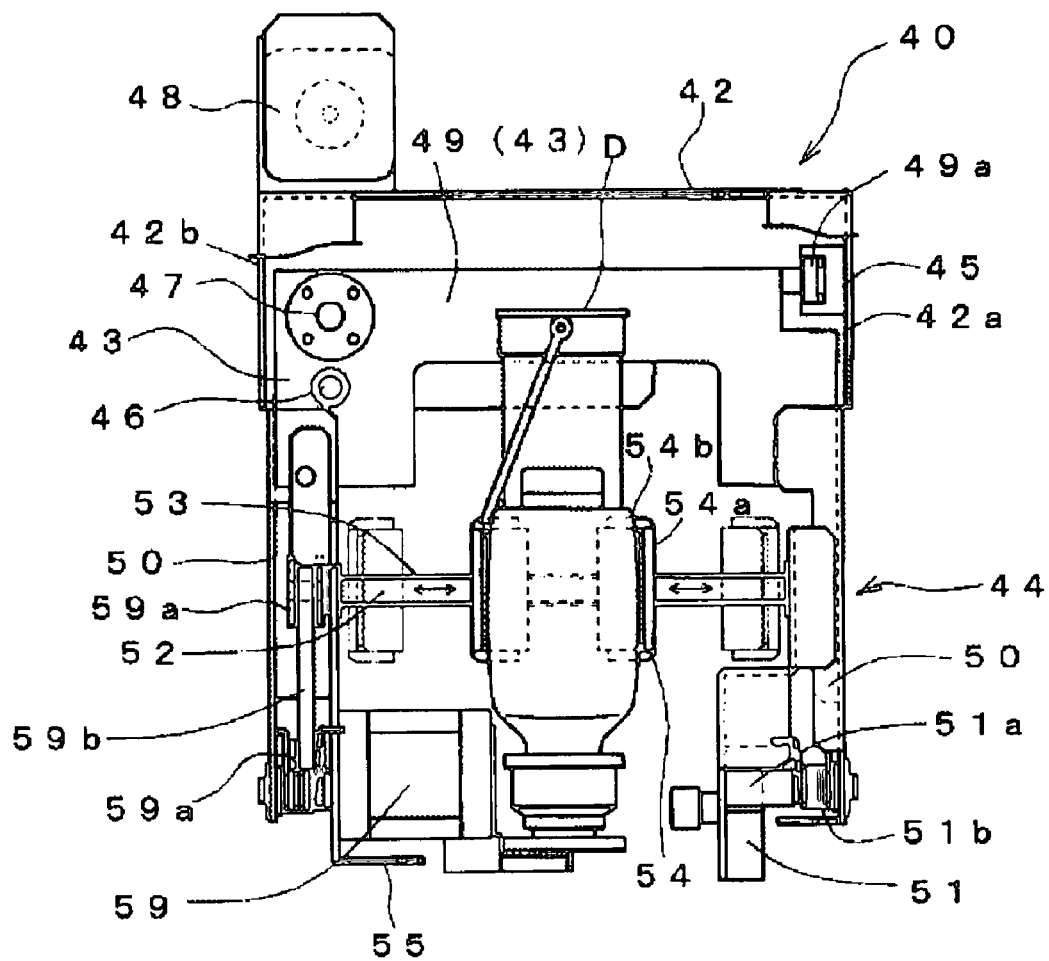
FIG. 5 is a front view of the holding member shown in FIG. 1.
Figure 6:
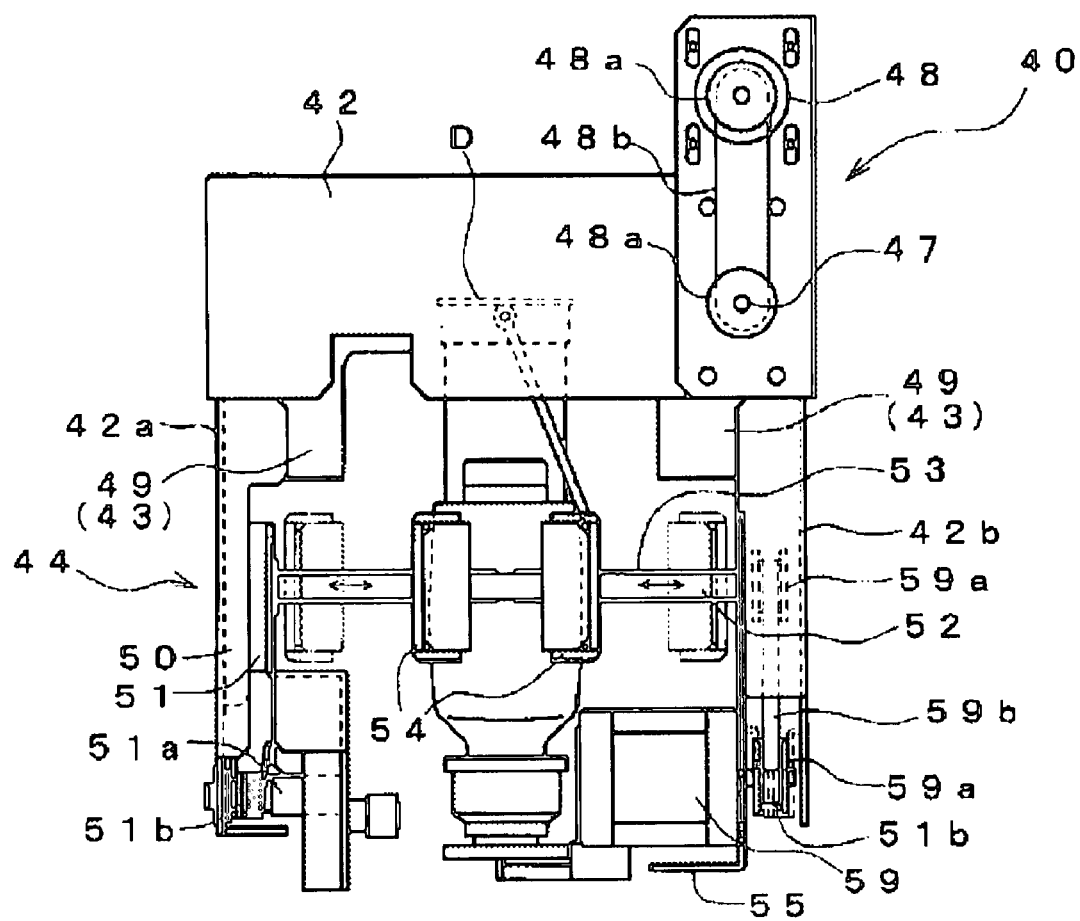
FIG. 6 is a rear view of FIG. 5.

Each holding member 54 is composed of an outer frame 54a adapted to guide in a rectangular form in side view in FIG. 5, and an elastic guide portion 54b integrated therein and held in press contact with the outer peripheral surface of the drug D. The elastic guide portion 54b is formed so as to exhibit a saw-tooth-like surface sectional configuration of the surface in contact with the drug D, thereby stabilizing the manner in which the drug D is held.

As shown in FIG. 1, the tray conveying line 4 is formed by a plurality of conveying rollers 60 arranged at predetermined intervals in the horizontal direction. The conveying rollers 60 are rotated by a motor or the like (not shown), and convey the tray 5 placed thereon. At one end of the tray conveying line 4, there is provided a stopper (not shown), causing the conveyed tray 5 to temporarily stop at a predetermined position and making it possible to dispense the drug D conveyed by the drug conveying member 3.

Figure 12:
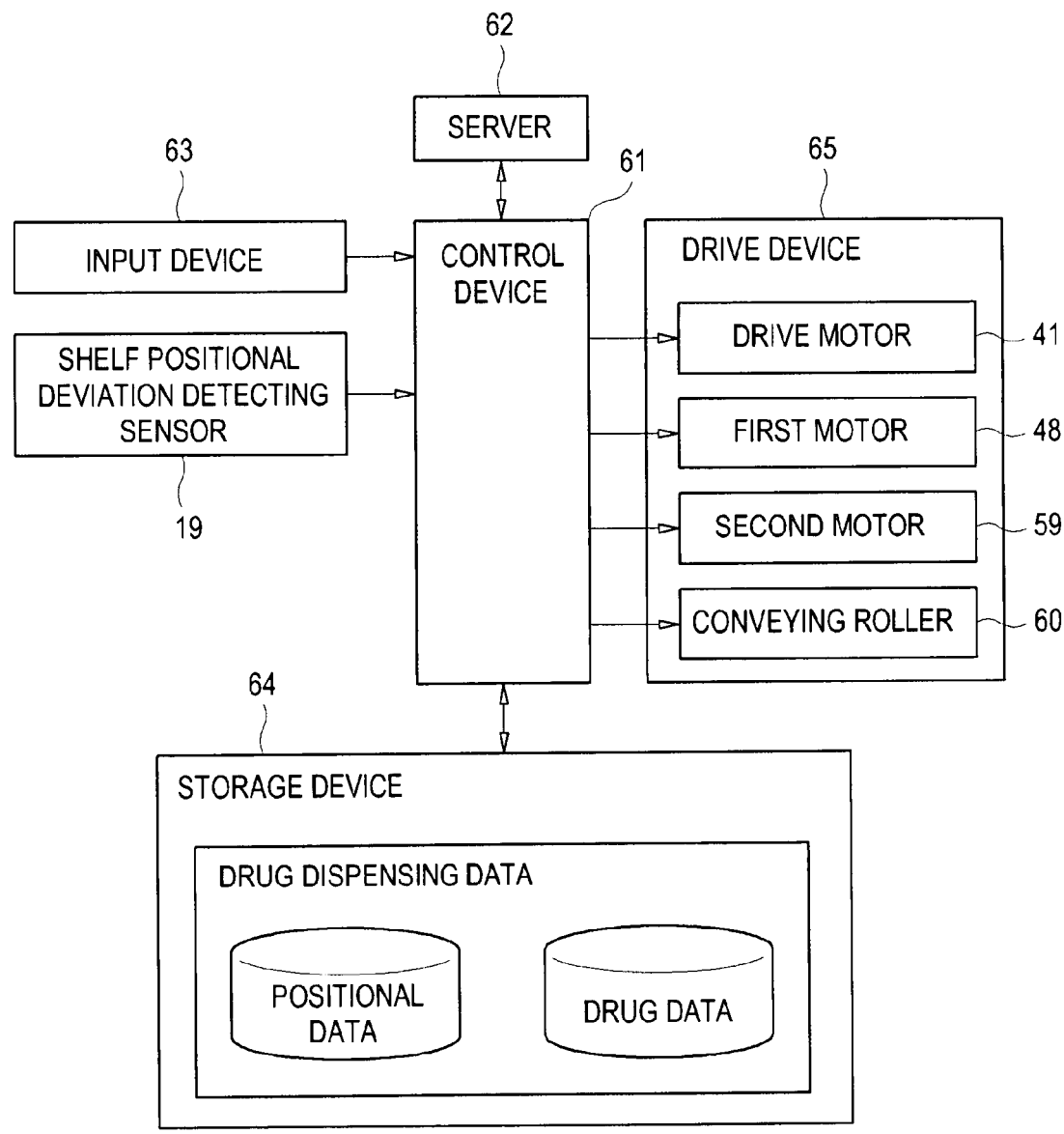
FIG. 12 is a block diagram showing the drug supply device of this embodiment of the present invention.

As shown in the block diagram of FIG. 12, in the drug dispensing device constructed as described above, a control device 61 makes reference to data stored in the storage device 64 based on prescription data input from a server 62 and an input device 63, a detection signal from the shelf positional deviation detecting sensor 19, etc., and drive-controls drive devices 65 such as motors.

The storage device 64 stores various items of drug dispensing data. The drug dispensing data includes position data, drug data, map data, etc. Here, the position data implies the position of the cassette 26 in the shelf member 2, etc. The drug data implies the kind, remaining amount, configuration, etc. of the drugs D accommodated in each shelf member 2.

The map data includes a container map and an article map (which, in this case, is a drug map). The container map is obtained by dividing the interior of the tray 5 into which the drugs D are to be delivered into a plurality of virtual regions (hereinafter referred to as container virtual regions), and imparting an identification number to each container virtual region. In the example of the container map shown in FIG. 16, identification numbers "1" through "60" are imparted in columns starting from the left, with the numbers in each column being successively arranged from below to above. The container virtual regions are all of the same size, and the container map is stored in the storage device 64 according to the kind of tray 5. Further, each container virtual region is associated with presence/absence data indicating whether a drug D accommodated is situated therein or not (For example, the presence data when a drug is present is indicated by the number "1", and the absence data when a drug is absent is indicated by the number "0").

The article map is obtained by sectioning each drug D accommodated in the tray 5 in the same size as the container virtual regions, and imparting an identification number to each virtual region (Hereinafter, the virtual regions of the drug map will be referred to as drug virtual regions). As in the case of the container map, in the example of the drug map shown in FIG. 16, identification symbols "a" through "n" are imparted in columns successively starting from the left, with the symbols in each column being successively arranged from below to above. However, as shown in FIG. 17, when setting the drug virtual regions for the drug D, there is adopted a pattern which is enlarged from the center of the right-hand edge by an amount corresponding to one drug virtual region as compared with the actual size of the drug D (The protrusion at the center of the upper edge corresponds to the configuration of the drug D). The provision of the protrusion is effected for the following reason: when accommodating the drug D in the tray 5, if there is any drug D previously accommodated, it is necessary to avoid interference with this drug D1 previously accommodated with the drug D2 to be accommodated next (or interference with the holding members 54 of the drug grasping member 40 for holding the drug D2), and to accommodate the drugs D smoothly in the tray 5.

While in the above-described embodiment the container virtual regions and the drug virtual region are of the same size, they may also be of different sizes if the correlation between these regions is a definite one. For example, the container virtual region may be of a size corresponding to a combination of a plurality of drug virtual regions, or the drug virtual region may be of a size corresponding to a combination of a plurality of container virtual regions. Further, the size and configuration of each virtual region can be set freely (e.g., a triangular configuration). In brief, any setting will do as long as the correlation between the container virtual regions and the drug virtual region is definite, and it is possible to check through searching whether it is possible to accommodate a drug in the container.

Figure 13:
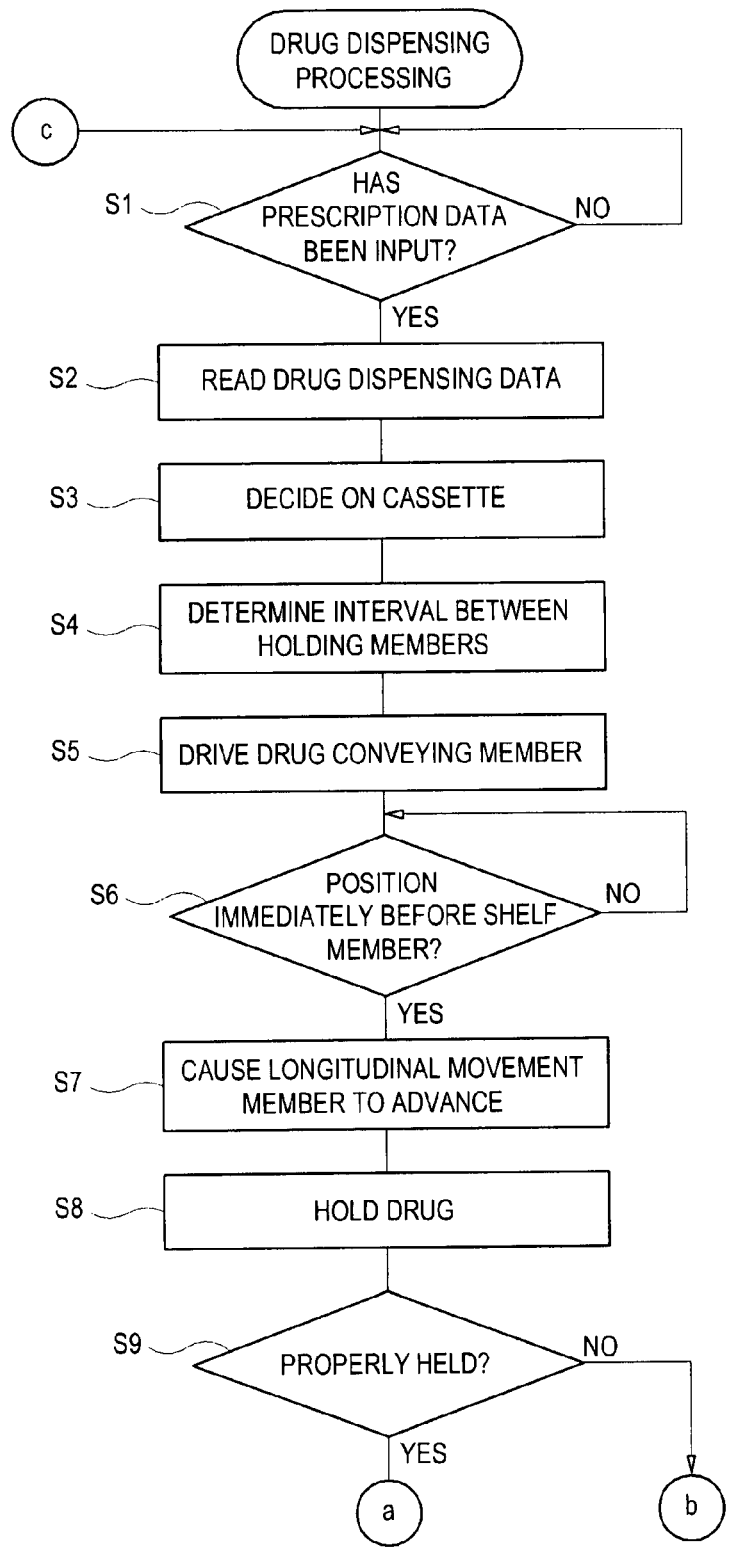
FIG. 13 is a flowchart illustrating the operation of the drug supply device of this embodiment of the present invention.
Figure 14:
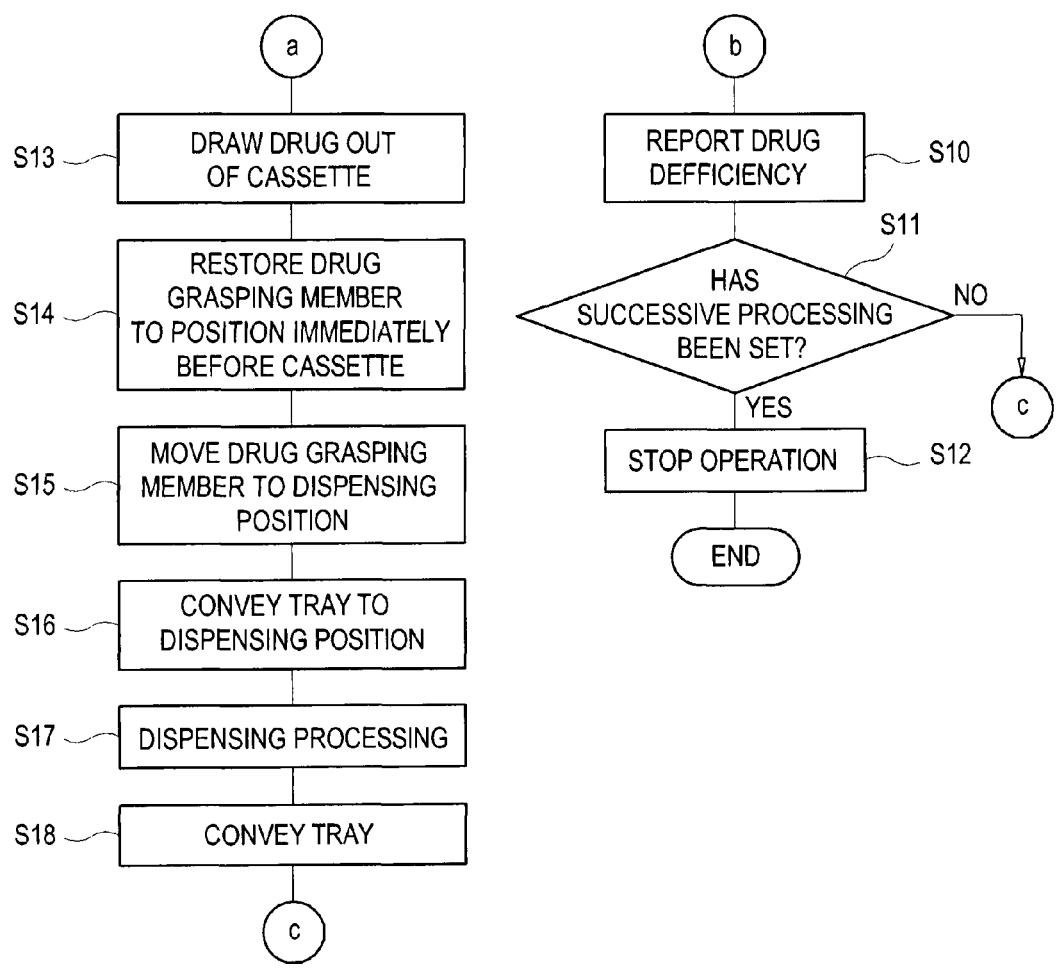
FIG. 14 is a flowchart illustrating the operation of the drug supply device of this embodiment of the present invention.

Next, the operation of the drug dispensing device, constructed as described above, will be illustrated with reference to the flowcharts of FIGS. 13 and 14.

When prescription data is input from the server 62 or the input device 63 (Step S1), drug dispensing data stored in the storage device 64 is read based on the input prescription data (Step S2). Then, based on the read drug dispensing data, the cassette 26 of the shelf member 2 from which the drug D included in the prescription data is to be extracted is determined (Step S3). Further, based on the configuration of the drug D included in the drug dispensing data, the distance between the holding members 54 is previously determined at a value slightly larger than the width dimension of the drug D (Step S4). As a result, it is possible to hold the drug D with a requisite minimum operation, with the drug grasping member 40 moved to a position immediately before the drug D, thus making it possible to reduce the operation time. Further, since the distance between the holding members 54 with respect to the width dimension of the drug D can be set to a requisite minimum level, it is possible to arrange the cassettes 26 in each shelf member 2 at the closest positions where they do not interfere with the holding members 54.

Subsequently, the drug conveying member 3 is driven to move the drug grasping member 40 to the shelf member 2 accommodating the corresponding drugs D (Step S5). Then, when the drug grasping member 40 moves to a position immediately before the shelf member 2 accommodating the corresponding drug D (Step S6), the first motor 48 is caused to make normal rotation to cause the longitudinal movement member 43 to advance (Step S7). Then, the second motor 59 is driven to hold the drug D with the holding members 54 (Step S8).

Here, a judgment is made as to whether the drug D has been properly held by the holding members 54 or not (Step S9). This judgment is made by detecting the state in which electricity is supplied to the second motor 59, checking whether there is an excessive current or not. When there is an excessive current and, for example, the detected voltage value is in excess of a preset threshold value, it is judged that the drug D is being held by the holding members 54. When the detected voltage value is not in excess of the threshold value, it is judged that nothing is being held by the holding members 54.

When it is judged that the drug D is not being properly held by the holding members 54, no drug D is judged to be accommodated in the corresponding cassette 26, and drug deficiency is reported (Step S10).

Here, a judgment is made as to whether successive processing has been set or not (Step S11). When no successive processing has been set, the operation is stopped (Step S12); when it has been set, the procedure returns to Step S1, and the above-mentioned processing is repeated.

When it is judged that the drug D has been properly held by the holding members 54, the drive motor 41 of the drug conveying member 3 is driven to make normal rotation, and causes the drug grasping member 40 to ascend, drawing the drug D held by the holding members 54 from cassette 26 (Step S13). Then, the first motor 48 is driven to make reverse rotation, and the drug grasping member 40 is returned to the position immediately before the cassette 26 (Step S14). At this time, within the cassette 26, the drug D advances while being pressurized by the pusher 31 that is urged by the constant force spring 32. Thus, the drug D abuts the inner surface of the forward end of the cassette 26, and is automatically set ready for the next dispensing operation.

Subsequently, the drug grasping member 40 is moved to a predetermined position in the tray conveying line 4 (Step S15). At this time, the tray 5 is conveyed along the tray conveying line 4, and is kept on standby at the above-mentioned position (Step S16).

In the drug grasping member 40, immediately before reaching the above-mentioned predetermined position, the pressurizing member abuts the pressure receiving member 55, whereby the swiveling plates 51 swivel. The swiveling position for the swiveling plates 51 is below the lowermost shelf member 2, thus avoiding their interference with the shelf member 2. Thus, the drug D held by the holding members 54 protrudes forwards while laid on its side and, starting herewith, the dispensing processing described below is executed (Step S17). As a result, it is possible for the drug D to be accommodated in the tray 5 while laid on its side while suppressing an increase in the longitudinal dimension of the space formed on the front side of the shelf member 2 inside the device main body 1.

When, from this onward, the dispensing of the drugs D included in the prescription data onto the tray 5 is completed in the same manner, the stopping of the tray 5 by the stopper along the tray conveying line 4 is canceled, and the tray 5 is conveyed from the device main body 1 to the exterior (Step S18).

In this way, according to the drug dispensing device of this embodiment, the arrangement position for the drug conveying member 3 and the position where the shelf 2 is drawn out to replenish the cassettes 26 with drugs D can be on the front side of the drug main body 1, so sharing of the same space is possible, thereby enabling to form the device itself compact. Further, in the drug conveying member 3, it is possible to swivel the holding members 54 below the shelf member 2 situated lowermost to thereby dispense the drug D held onto the tray 5, so an increase in space formed between the shelf member 2 and the front surface of the device main body 1 can be suppressed. Further, the shelf member 2 can be drawn out obliquely downwards, so, even in the case of the first shelf member 2a situated uppermost, it is possible to easily perform the filling of the cassettes 26 with the drugs D.

Figure 15A:
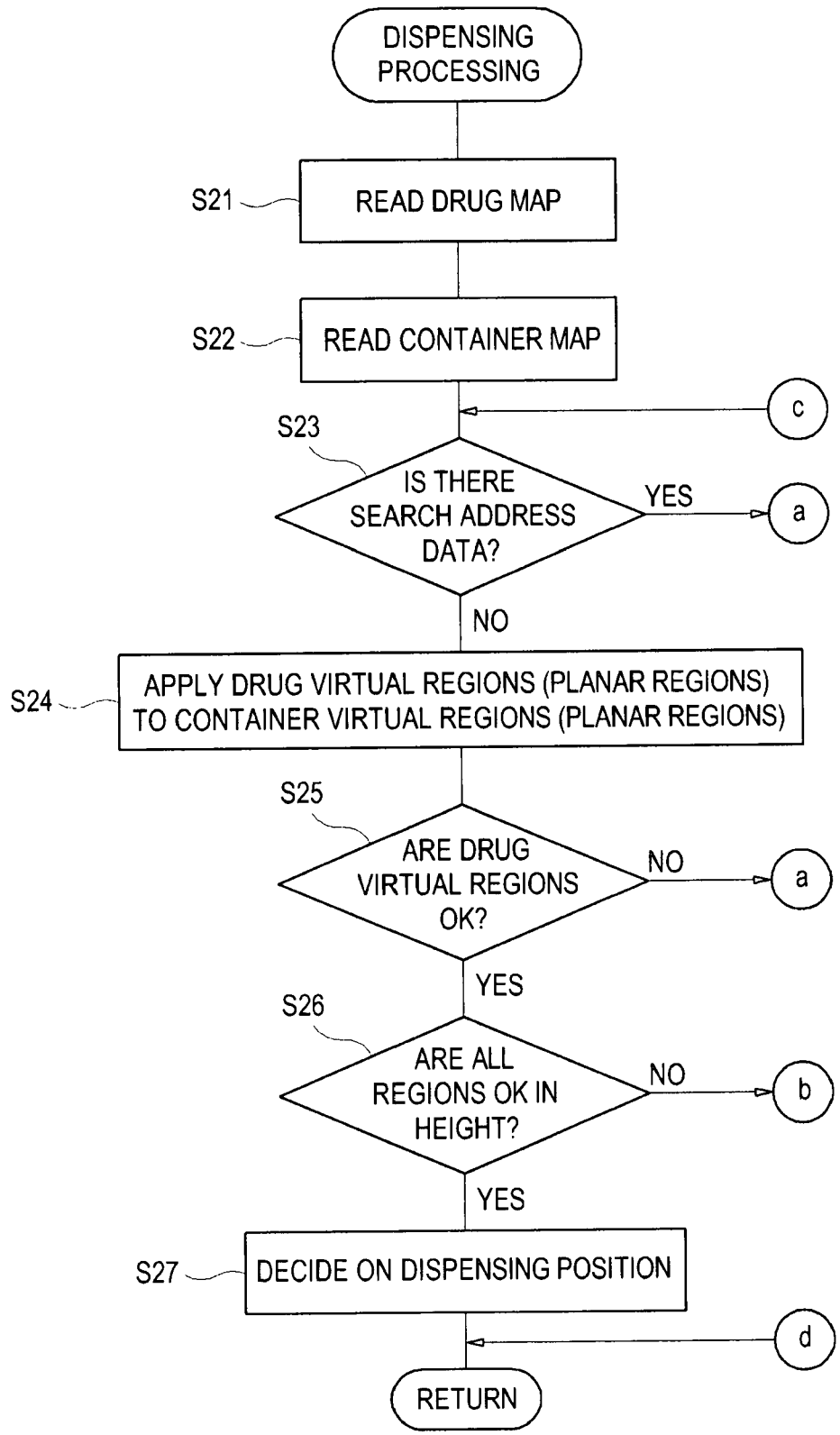
FIG. 15A is a flowchart illustrating the dispensing processing of FIG. 14.

The dispensing processing to dispense the drug D onto the tray 5 by the drug grasping member 40 is executed according to the flowcharts shown in FIGS. 15A and 15B.

That is, the drug map is read from the storage device 64 with respect to the drug D to be dispensed onto the tray 5 (Step S21). Further, the container map of the tray 5 is read (Step S22). Then, it is checked whether there is any data of the search address in descending order of the identification numbers imparted to the container virtual regions (Step S23). When there is no data of the search address, all of the drug virtual regions are applied to the corresponding container virtual regions (Step S24), making a judgment as to whether arrangement is possible or not (Step S25).

When any one of the corresponding virtual regions of the container map exhibits presence data and is judged to be not vacant, it is impossible to dispense a drug D to that position. When it is judged in Step S23 that there is data of the search address, or when it is judged in Step S25 that it is impossible to apply all of the drug virtual regions to the corresponding container virtual regions, a drug D cannot be arranged at that position. In view of this, 1 is added to the number i affixed to the address constituting the object of search (Step S28), and the procedures of Step S S23 through S25 are repeated until search is completed on all of the container virtual regions, that is, until i becomes 60 (Step S29).

When a space allowing arrangement of a drug D cannot be detected even after search has been completed on all of the container virtual regions, 1 is added to a stage t, and search processing is executed at a level one stage higher (Step S30). This processing is conducted within a range in which the number of stages s to be searched does not attain 4 (s<4) (Step S31).

Then, when it is judged that the corresponding container virtual regions are vacant for all the drug virtual regions, a judgment is made as to whether the upper stage is also vacant or not for all the container virtual regions judged to be vacant (Step S26). That is, in the case in which this judgment is made at the first stage, a judgment is also made likewise for the second stage onward as to whether each container virtual region exhibits absence data or not (Step S32). This judgment from the second stage onward is also made since, when dispensing a plurality of kinds of drugs D of fixed priority order onto one tray 5, a case is expected in which even when the first stage provides a vacant region, the second stage is not vacant. For example, when accommodating two kinds of drugs D of a rectangular configuration in plan view in two upper and lower stages, if the occupation area of the drug D accommodated in the first stage is smaller than that of the drug D accommodated in the second stage, there is a possibility that even if the first stage container virtual region exhibits absence data, the corresponding second stage virtual region exhibits presence data; this is why the judgment in Step S26 is made.

The judgment in Step S26 is similarly made even when the drug D has a height dimension covering a plurality of stages. In this case, however, it is also necessary to make a judgment as to whether the uppermost stage of the drug D can be accommodated in the tray 5 or not.

This processing is conducted within a range in which the drug height is not in excess of the container height (Step S33). Here, search processing is conducted within a range in which the number of stages s to be searched does not attain 4 (s<4).

In this way, when it is determined that there is a space available allowing arrangement also in the height direction, dispensing of a drug D to that position is decided on (Step S27).

When, in Step S S29 through S31, no space allowing arrangement of a drug D is detected until search has been conducted on all of the container virtual regions, or, when, in Step S33, no space allowing arrangement of a drug D in the height direction is detected, an error processing is executed, or transition is effected to dispensing onto the next tray (Step S34).

As described above, also when the next drug D is to be dispensed onto the same tray 5, search is conducted on the container virtual regions in descending order starting from the first position (i=1), so, if the kind of drug differs or the dispensing order differs, it is possible to effect arrangement at high density. In particular, this dispensing control method proves effective in that it can be flexibly applied also to a case in which drugs D of different sizes and forms are to be dispensed.

More specifically, a case will be described in which the drugs (which, in this case, are drugs in the form of 500 ml bottles) of the drug map shown in FIG. 17 are to be dispensed into the tray 5 of the container map shown in FIG. 16. When dispensing the first drug D1, all the container virtual regions are vacant. Thus, the first identification numbers/symbols in descending order (the container virtual region "1" and the drug virtual region "a") correspond to each other without fail, and the dispensing position is settled on the shaded portion in FIG. 18.

Subsequently, when dispensing the second drug D2, search of the container virtual regions of the container map in descending order shows that the identification symbol "a" of the drug virtual regions is applicable to the identification number "5". However, no drug virtual region exists at the position corresponding to the identification symbol "b". Thus, the dispensing position is not decided upon. If the identification symbol "a" is successively applied to the identification numbers "6" through "20", the dispensing position cannot be specified. By applying the identification symbol "a" of the drug virtual region to the identification number "21", it is possible to apply all the drug virtual regions of the drug map to the vacant regions of the container map. Thus, the dispensing position is settled upon this position.

Figure 20:
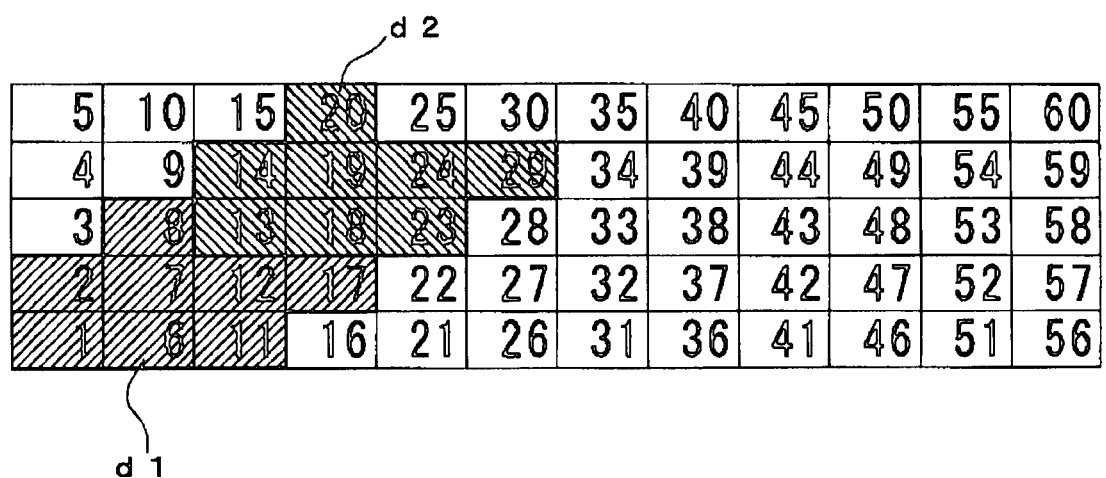
FIG. 20 is a diagram illustrating how the drug map shown in FIG. 19 is applied to the container map of FIG. 16.

When dispensing the drugs D (which, in this case, are drugs in the form of 100 ml bottles) of the drug map shown in FIG. 19, the dispensing position for the second drug d2 is determined with respect to the first drug d1 as shown in FIG. 20. As a result, it is possible, instead of dispensing the drugs in a single horizontal row, to dispense them while alternately shifting their positions in the vertical direction. That is, the drugs D are accommodated at high density in the limited space in the tray 5.

The operation of dispensing the drugs D onto the tray 5 is conducted as described above. In the case where the tray 5 is of a construction allowing accommodation of the drugs D in a plurality of stages, when no drug D can be accommodated in the first stage, detection of a vacant region is conducted in the same manner for the second stage onwards to settle on the dispensing position.

When there exists no more drug D in the shelf member 2, the shelf member 2 is drawn out to replenish it with drugs D. That is, by pulling the lock member 23, the lock portion 24 thereof is detached from the locking/receiving portion 17 of the device main body 1, and the shelf member 2 is drawn out by grasping the grip 22. As shown in FIG. 2 or 3, in the case where the shelf to be drawn out is the uppermost shelf member 2, it is possible to tilt the forward, drawn-out side thereof downwardly after drawing it out of the device main body 1. More specifically, when the shelf member 2 is pulled by grasping the grip 22, the first rail portion 13 and the second rail portion 14 expand successively on the side wall, and the guide roller 25 slides on the first guide surface 9, whereby the shelf member 2 moves horizontally toward the front side. When the guide roller 25 reaches the second guide surface 10, the guide by the first guide surface 9 is lost, so the shelf member 2 can be rotated around the support shaft 16. Thus, when the shelf member 2 is rotated against the urging force of the spring 16a, the guide roller 25 rolls on the second guide surface 10, and the drawn-out side (forward end side) is tilted so as to be downwardly oblique. By being tilted to a predetermined position, the shelf member 2 is prevented from rotating by the lock member 23, so the cassettes 26 are filled with drugs D.

In accommodating drugs D in the cassette 26, the pusher 31 of the drug extraction member 30 is pressed and moved toward the rear end against the urging force of the constant force spring 32, and the lock claw 37 of the lock lever 33 is locked to the lock hole 29 formed on the back side of the cassette 26. When the replenishment of the cassette 26 with the drug D is completed, the lock lever 33 is operated to detach the lock claw 37 from the lock hole 29, and the drug D is moved to the front side of the cassette 26 by the urging force of the constant force spring 32 for alignment.

The numerical references herein identify the various items as follows:

1: device main body
    2: shelf member
    2a: first shelf member
    2b: second shelf member
    3: drug conveying member (dispensing means)
    4: tray conveying line
    5: tray
    6: guide member
    6a: first guide member
    6b: second guide member
    7: guide wall
    7a: guide groove
    8: guide rail
    9: first guide surface
    10: second guide surface
    11: support roller
    12: lock protrusion
    13: first rail portion
    14: second rail portion
    15: support wall
    15a: abutment/receiving portion
    16: support shaft
    16a: spring
    17: locking/receiving portion
    18: support rail portion
    19: shelf positional deviation detecting sensor
    20: box body
    21: drug accommodating portion
    22: grip
    23: lock member
    24: lock portion
    25: guide roller
    26: cassette
    27: groove portion
    28: support plate
    29: lock hole
    30: drug extrusion member
    30a: casing
    31: pusher
    31a: protrusion
    32: constant force spring
    33: lock lever
    34: drum
    35: spring portion
    36: operating portion
    37: lock claw
    38: horizontal guide bar
    39: vertical guide bar
    40: drug grasping member 41: drive motor
41a: pulley
41b: belt
42: support member
43: longitudinal movement member
44: holding member
45: guide receiving portion
46: first guide shaft
47: first screw
48: first motor
48a: pulley
48b: belt
49: slide stand
49a: roller
50: side plate portion
51: swiveling plate
52: second guide shaft
53: second screw
54: holding member
54a: outer frame
54b: elastic guide portion
55: pressure receiving member
56: first lock plate
56a: roller
56b: lock pin
57: second lock plate
58: lock hole
58a: arcuate portion
58b: first lock recess
58c: second lock recess
59: second motor
59a: pulley
59b: belt
60: conveying roller
61: control device (control means)
62: server
63: input device
64: storage device
65: drive device
D: drug
d1: body portion
d2: leg portion

The invention claimed is:

1. An article dispensing device comprising:
a device main body;
a drug conveying member for holding and dispensing articles one after another, the drug conveying member being coupled with the device main body and including a drug grasping member for holding the articles;
a container for containing the articles dispensed by the drug conveying member one after another, wherein each of the articles includes a different size and form;
a storage device for storing a container map and a plurality of article maps, wherein the container map defines an internal space of the container as a plurality of container virtual regions and each of the article maps defines the article as a plurality of article virtual regions in accordance with the size and form thereof; and
a control device for accessing the storage device to recall the article map having the plurality of the article virtual regions of one article to be dispensed within the container by the drug conveying member and the container map, the control device being capable of searching for at least one vacant container virtual region in terms of the article map of said one article to be dispensed within the container and specifying the searched vacant container virtual region as a dispensing position within the container for said one article by referring to the container map and the article map stored in the storage device, wherein the control device drive-controls the drug conveying member based on the specified dispensing position for said one article to be dispensed within the container by the drug conveying member in the container.

2. An article dispensing device according to claim 1, wherein a size of one among the container virtual regions corresponds to a size of one or more article virtual regions, or a size of one or more among the article virtual regions corresponds to a size of one or more of the container virtual regions.

3. An article dispensing device according to claim 1, wherein the article map stored in the storage device includes at least a stick-out region for avoiding interference between the articles.

4. An article dispensing device according to claim 1, wherein the articles are contained in the container vertically in a plurality of stages, the container map stored in the storage device defining a container virtual space in three-dimensional space sectioned vertically in the container, the article map stored in the storage device defining article virtual spaces of the respective articles to be contained in the container one after another, and
wherein the storage device stores instructions executable by the control device, the instructions comprising:
(a) determining if the article virtual space of one article to be contained in the container occupies a plurality of vertical sections in the container virtual space, wherein the article virtual space of said one article to be contained in the container includes a first virtual section on a lower stage and a second virtual section on an upper stage,
(b) searching vacant vertical sections in the container virtual space if article virtual space of said one article to be contained in the container occupies the plurality of vertical sections,
(c) checking whether the vacant vertical sections include a first vacant section having the same size as the first virtual section on the lower stage and a second vacant section having the same size as the second virtual section on the upper stage, and
(d) establishing the vacant vertical sections as a dispensing position when the first and second vacant sections have the same sizes as the first virtual section on the lower stage and the second virtual section on the upper stage.

5. An article dispensing device according to claim 2, wherein the article map stored in the storage device stores at least a stick-out region for avoiding interference between the articles.

6. An article dispensing device according to claim 2, wherein the articles are contained in the container vertically in a plurality of stages,
the container map stored in the storage device defines a container virtual space in three-dimensional space sectioned vertically in the container, and
the article map defines article virtual spaces the respective articles to be contained in the container one after another, and
wherein the storage device stores instructions executable by the control device, the instructions comprising:
(a) determining if the article virtual space of one article to be contained in the container occupies a plurality of vertical sections in the container virtual space, wherein the article virtual space of said one article to be contained in the container includes a first virtual section on a lower stage and a second virtual section on an upper stage,
(b) searching vacant vertical sections in the container virtual space if the article virtual space of said one article to be contained in the container occupies the plurality of vertical sections,
(c) checking whether the vacant vertical sections include a first vacant section having the same size as the first virtual section on the lower stage and a second vacant section having the same size as the second virtual section on the upper stage, and
(d) establishing the vacant vertical sections as a dispensing position when the first and second vacant sections have the same sizes as the first virtual section on the lower stage and the second virtual section on the upper stage.

7. An article dispensing device according to claim 3, wherein the articles are contained in the container vertically in a plurality of stages,
the container map stored in the storage device defines a container virtual space in three-dimensional space sectioned vertically in the container, and
the article map defines article virtual spaces the respective articles to be contained in the container one after another, and
wherein the storage device stores instructions executable by the control device, the instructions comprising:
(a) determining if the article virtual space of one article to be contained in the container occupies a plurality of vertical sections in the container virtual space, wherein the article virtual space of said one article to be contained in the container includes a first virtual section on a lower stage and a second virtual section on an upper stage,
(b) searching vacant vertical sections in the container virtual space if the article virtual space of said one article to be contained in the container occupies the plurality of vertical sections,
(c) checking whether the vacant vertical sections include a first vacant section having the same size as the first virtual section on the lower stage and a second vacant section having the same size as the second virtual section on the upper stage, and
(d) establishing the vacant vertical sections as a dispensing position when the first and second vacant sections have the same sizes as the first virtual section on the lower stage and the second virtual section on the upper stage.

8. An article dispensing method for an article dispensing device including a drug conveying member, a container, a storage device and a control device, the method comprising the steps of:
preparing a container map defining an internal space of the container as a plurality of container virtual regions in the storage device;
preparing a plurality of article maps of articles in the storage device, wherein each of the articles includes a different size and form and each of the article maps includes at least one article virtual region in accordance with the size and form of the article;
searching for at least one vacant container virtual region in terms of the article map of one article to be dispensed within the container by using the control device;
specifying the searched vacant container virtual region as a dispensing position for said one article to be dispensed within the container by the drug conveying member by referring to the container map and the article map by using the control device; and
dispensing said one article at the dispensing position by using the drug conveying member.

* * * * *